United States Patent [19]

Koch et al.

[11] 4,309,547

[45] Jan. 5, 1982

[54] PROCESS FOR THE PREPARATION OF PHENOXYPROPIONIC ACIDS AND THEIR ALKALI METAL SALTS

[75] Inventors: Manfred Koch, Eppstein; Hans J. Nestler, Königstein, both of Fed. Rep. of Germany

[73] Assignee: Hoechst Aktiengesellschaft, Frankfurt am Main, Fed. Rep. of Germany

[21] Appl. No.: 155,009

[22] Filed: May 30, 1980

[30] Foreign Application Priority Data

Dec. 11, 1979 [DE] Fed. Rep. of Germany ....... 2949728

[51] Int. Cl.³ .................................... C07D 213/44
[52] U.S. Cl. .................................. 546/301; 71/94; 71/114; 546/335; 560/61; 560/62; 562/471; 562/472

[58] Field of Search ............... 562/471, 472; 546/301, 546/335; 560/61, 62

[56] References Cited

U.S. PATENT DOCUMENTS

| | | | |
|---|---|---|---|
| 3,968,143 | 7/1976 | Schact et al. | 562/471 X |
| 4,134,753 | 1/1979 | Horlein et al. | 562/471 X |
| 4,153,803 | 5/1979 | Thiele et al. | 562/471 X |
| 4,173,709 | 11/1979 | Metivier et al. | 562/471 O |

*Primary Examiner*—John D. Randolph
*Attorney, Agent, or Firm*—Curtis, Morris & Safford

[57] ABSTRACT

Process for the preparation of (phenoxy- or benzyl-)-phenoxypropionic acids by simultaneous addition of 2-chloropropionic acid (ester) and the double molar amount of an aqueous alkali hydroxide to a solution of a phenoxyphenol or benzylphenol in a solvent forming an azeotropic mixture with water, while continuously distilling off the water formed or introduced.

1 Claim, No Drawings

PROCESS FOR THE PREPARATION OF PHENOXYPROPIONIC ACIDS AND THEIR ALKALI METAL SALTS

It is known that alkyl- and/or halogen-substituted phenoxy-alkanecarboxylic acids which are of great economic importance as hormone-type herbicides are obtained by reaction of alkali phenolates with alkali salts of corresponding 2-haloalkanecarboxylic acids.

The reaction is generally carried out by condensing alkali phenolate and alkali-2-haloalkanecarboxylate in a molar ratio of 1:1 in water as solvent or diluent (see G. Erfurt et al., Chem. Technik 15 (1964), No. 4, p. 199; GDR Pat. Nos. 64,279, 64,972, 64,723).

Because of inevitable side reactions, mainly hydrolysis of haloalkanecarboxylate to hydroxyalkanecarboxylate, the yield is not satisfactory (70–80% of theory). The yield is even more reduced if the reaction is transferred from 2-chloroacetic acid to higher 2-chloroalkanecarboxylic acids such as 2-chloropropionic and 2-chlorobutyric acid (German Pat. No. 1,153,762).

The yield of hormone-type herbicides can be increased by suppressing the hydrolysis to a certain extent, for example according to the following methods:

(a) Use of anhydrous reactants (U.S. Pat. No. 2,651,659). Although considerably increased yields are obtained according to this process, it is unfit for application on an industrial scale because
preparation of anhydrous agents, especially of alkali metal salts of 2-haloalkanecarboxylic acids sensitive to hydrolysis, is difficult and expensive,
large volumes of organic solvents are required,
solids and suspensions are difficult to dose, and
considerable amounts of lactates are formed as undesirable by-products because of side reaction of phenoxyalkanecarboxylic acid salts with haloalkanecarboxylic acid salt.

(b) Partial replacement of water as solvent and diluent by high-boiling alcohols (German Pat. No. 1,153,762, U.S. Pat. No. 2,914,558, USSR Pat. No. 187,766, Japanese patent application No. 48,705/65), hydrocarbons (U.S. Pat. No. 2,480,817), or excess free phenol (U.S. Pat. No. 4,035,496, GDR Patent No. 50,622).

(c) Use of alkali metal phenolate in an excess of up to 100%, relative to 2-haloalkanecarboxylic acid salt, in order to increase the speed of the main reaction as compared to that of the side reaction (U.S. Pat. Nos. 4,035,416 and 3,257,453, German Pat. No. 1,153,762, Japanese Pat. Publication No. 74/24463).

(d) Reduction of the water amount present in the reaction mixture by distilling off water during the reaction (U.S. Pat. No. 4,035,416).

It is further known from German Auslegeschrift No. 15,43,841 to prepare optically active hormone-type herbicides by condensation of alkali phenolates and alkali salts of L-2-chloropropionic acid in hydrocarbons such as toluene, i.e. according to the method cited in (c). The yield of optically active acid is reported to be 85–90%.

All processes for the preparation of hormone-type herbicides hitherto known have the following characteristic features in common:

(1) The amount of phenol to be used in the reaction is introduced into the reaction vessel in the form of alkali phenolate, and 2-haloalkanecarboxylic acid salt is added in one portion, in dosed amounts or continuously. In some cases, the alkali amount required in total is introduced as excess alkali phenolate or as a mixture of alkali phenolate and alkali hydroxide, and free 2-haloalkanecarboxylic acid is added.

(2) The phenol component is not reacted quantitatively. Separation and recovery of unreacted phenol is required after completion of the reaction.

However, phenoxypropionic acids of the formula I (see below) cannot be obtained industrially in a similar manner, because the starting phenols of the formula II (also described below) cannot be separated from the compounds of the formula I except by complicated and time-consuming purification operations resulting in great losses.

For the preparation of the formula I compounds various process variations have been described which, however, do not lead to quantitative yields either. For example, German Offenlegungsschrift No. 16,68,896 describes among others the reaction of alpha-haloalkanecarboxylic acids with phenoxyphenols in aqueous, strongly alkaline solution. When operating according to this method, which corresponds to the early state of hormone-type herbicide manufacture, by condensing phenoxyphenols with a 20 molar % excess of L-2-chloropropionic acid in an aqueous, strongly alkaline solution, a yield of only 82% of theory is obtained. A conversion rate of more than 95% of the phenol component is achieved only with a considerably increased excess of L-2-chloropropionic acid (more than 40%). Such a process is unfit for quantitatively converting phenols of the formula II on an industrial scale.

Improvement of this reaction by replacing water as solvent or diluent by a hydrocarbon such as toluene or xylene and azeotropic distillation of water during the reaction (as described in (b) and (d) above) likewise does not result in quantitative yields. Thus, use of an excess of 20% of 2-chloropropionic acid (relative to the amount of phenol used) yields a conversion rate of 92–93% of the phenol component only.

It has now been found that the disadvantages of the processes as described above can be overcome by using free phenols instead of alkali phenolates and by simultaneously adding alkali chloropropionate and alkali hydroxide. In this way, alkali phenolate is formed in situ and immediately reacts with the chloropropionate. An excess of alkali hydroxide, which would result in partial hydrolysis of 2-chloropropionic acid to lactic acid, is thus considerably reduced during the main reaction.

Subject of the present invention is therefore a novel semicontinuous process for the preparation of phenoxypropionic acids and the alkali metal salts thereof corresponding to the formula I

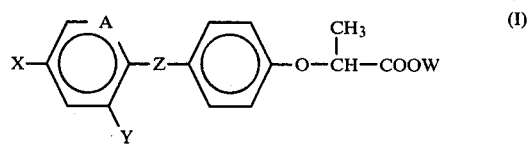

in which

W is hydrogen or an alkali metal cation, and Z is oxygen or $CH_2$, and in the case where Z is O, X is Cl, Br or $CF_3$; A is —N= or —CH=; and Y is H or Cl; and in the case where Z is $CH_2$, X is Cl; A is —CH= and Y is H or Cl; and their optically active D-isomers, which comprises adding to a compound of the formula II

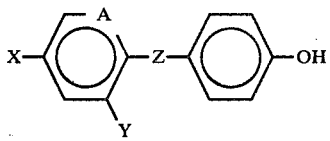
(II)

in which A, X, Y and Z are as defined above, 2-chloropropionic acid or 2-chloropropionic acid lower alkyl ester or the D-isomers thereof, in a solvent forming an azeotropic mixture with water, at reflux temperature, and the double molar amount, relative to the chloropropionic acid component, or a slight excess thereover, of aqueous alkali hydroxide, while simultaneously distilling off the water introduced or formed during the reaction.

2-Chloropropionic acid and alkali (preferably a 30–50% sodium hydroxide solution is used) are either added separately or are combined before addition to II, thus forming alkali-2-chloropropionate. The alkali-2-chloropropionate can be obtained also by saponification of 2-chloropropionic acid lower alkyl ester with excess alkali hydroxide and the reaction solution subsequently be added to the phenol of the formula II. Alternatively, 2-chloropropionic acid ester and alkali hydroxide may be added separately but simultaneously to the phenol. In this case, the ester is saponified first in situ to form 2-chloropropionate which then reacts with II.

Per mol of II, the 1.0- to 1.4-molar amount of 2-chloropropionic acid (ester) is used. For quantitative conversion an excess of at least 10%, preferably 12 to 25%, should be employed.

Advantageously, the reaction is carried out with the minimum amount or a small excess (up to 10%) of alkali metal hydroxide; however, a higher excess does not reduce the yield significantly. Preferably, NaOH is used as alkali metal hydroxide; KOH being also suitable.

Suitable solvents or diluents are hydrocarbons distilling as azeotropic mixture with water, preferably aromatic hydrocarbons such as benzene, toluene or chlorobenzene; especially preferred are xylene or toluene.

The reaction is carried out as follows: The compound of the formula II is dissolved in the solvent or diluent, the amount of which is chosen in such a manner that the reaction mixture can be easily stirred still at the end of the reaction time (generally, from about 0.3 to 3 liters per mol of II are used). 2-Chloropropionic acid (ester) and alkaline lye are added simultaneously or separately (or alternatively the solution of sodium-2-chloropropionate and alkali metal hydroxide) in such a manner that the water introduced into the reaction mixture or generated therein by salt formation is constantly distilled off as an azeotropic mixture. The amount of water present in the reaction mixture should preferably not exceed 2.5%, relative to the weight of the reactants used.

According to a variation of the process, 1.0 to 1.4 molar equivalents of 2-chloropropionic acid ester (preferably the methyl ester) and 2.0 to 2.8 molar equivalents of a 20–60%, preferably 25–50% aqueous alkali hydroxide solution are added about simultaneously with vigorous stirring from two separate vessels to the solution of the phenol at about boiling temperature. Feed rate and reaction temperature are adjusted in such a manner that the total amount of water introduced and formed in the reaction corresponds substantially to the amount of water removed by azeotropic distillation. The alcohol formed by saponification of the ester is distilled off with the water to a large extent.

During the reaction the temperature should be maintained between the boiling point of the pure solvent as upper limit and the boiling point of the solvent/water mixture; the reaction preferably being carried out at the lower temperature limit. In the case of xylene, the reaction temperature is from about 106° to 115° C.; with benzene, it is preferably from 74° to 80° C., and with toluene it is preferably 100° to 110° C.

After the end of the addition, stirring is continued for about 15 to 30 minutes at constant temperature in order to complete the reaction; subsequently the sodium salts of the phenoxypropionic acids formed are converted to the free acids by acidification with a mineral acid. The inorganic salts and the lactic acid present in the reaction mixture are eliminated by extraction with water.

After distilling off the solvent the compounds of formula I (W=H) are obtained with a yield of 99.5 to 99.9% of theory; the residual content of starting material of formula II is less than 0.5%. When using an optically pure L-2-chloropropionic acid or a lower alkyl ester, the optical purity of the D-(phenoxy or benzyl)-phenoxypropionic acids is from 86 to 92% of theory, corresponding to a content of from 93 to 96% of pure D-isomers.

The compounds of the formula I are highly active weed herbicides or intermediates for other acid derivates, for example esters, which are likewise very efficient, selective weed herbicides (German Offenlegungsschriften Nos. 22,23,894; 24,33,067; 26,01,548; 24,17,487 and 27,58,002).

The following Examples illustrate the invention, the parts being by weight unless otherwise stated.

EXAMPLE 1

2-[4'-(2",4"-Dichlorophenoxy)-phenoxy]-propionic acid

118 Parts of 50% sodium hydroxide solution are added with external cooling to 127.2 parts of 2-chloropropionic acid (98% strength) and 80 parts of water (or ice) in such a manner that the inner temperature does not exceed 40° C. The viscous liquid so obtained is added portionwise at 115° C. to a solution of 255 parts of 4-(2',4'-dichlorophenoxy)-phenol oxy)-phenol in 900 parts of toluene. By azeotropic distillation of water in a water trap, the reaction temperature is maintained at 115° C. during this addition. The addition being complete, stirring is continued for 15 minutes at 105° C., the batch is cooled to 90° C. and, after addition of 400 parts of water, stirred for 20 minutes at 85° C. Subsequently, the batch is acidified at 85° C. with 120 parts of phosphoric acid, stirred for 10 minutes, and the water phase is then separated. Toluene is distilled off in a water jet vacuum, and the solids obtained are dried at 80° C. and 250 mbar. 327 parts of 2-[4'-(2",4"-dichlorophenoxy)-phenoxy]-propionic acid are obtained. According to gas chromatography, the content of pure final product is 99.5%, corresponding to a yield of 99.5% of theory. The residual amount of 4-(2',4'-dichlorophenoxy)-phenol is 0.4%.

EXAMPLE 2

2-[4'-(4"-Trifluoromethylphenoxy)-phenoxy]-propionic acid 132.5 Parts of 2-chloropropionic acid (98% strength) and 199 parts of 50% sodium hydroxide solution are added simultaneously but separately at 110°-115° C. to a solution of 254 parts of 4-(4'-trifluoromethylphenoxy)-phenol in 1,000 parts of xylene. During the addition, the reaction temperature is maintained by azeotropic distillation of water in a water trap. The addition being complete, stirring is continued for 15 minutes at 110°-115° C., the batch is cooled to 90° C. and after addition of 400 parts of water, it is stirred for a further 10 minutes at 85° C., then acidified at this temperature with 120 parts of phosphoric acid, and stirred for a further 10 minutes. After elimination of the water phase, xylene is distilled off in a water jet vacuum, and the solids are dried at 60° C. and 250 mbar. 326 parts of 2-[4'-(4''-trifluoromethyl-phenoxy)-phenoxy]-propionic acid are obtained. The content of pure final product is 99.6% corresponding to a yield of 99.6% of theory. The residual content of 4-(4'-trifluoromethyl-phenoxy)-phenol is 0.35%.

EXAMPLE 3

129.8 Parts of 2-chloropropionic acid, 194 parts of 50% sodium hydroxide solution and 80 parts of water are mixed as described in Example 1. The clear, viscous liquid so obtained is added portionwise to a solution of 218.5 parts of 4-(4'-chlorobenzyl)-phenol in 1,000 parts of xylene; the reaction temperature being maintained at 110°-115° C. by azeotropic distillation of water in a water trap. The addition being complete, stirring is continued for 15 minutes at 110° C. Work-up is as described in Example 2. 290.5 Parts of 2-[4'-(4''-chlorobenzyl)-phenoxy]-propionic acid are obtained. The content of pure final product is 99.8%, corresponding to a yield of 99.8% of theory. The residual content of 4-(4'-chlorobenzyl)—phenol is 0.1%.

In analogous manner, there were prepared:

|  | Yield (% of th.) | Residual content of starting material |
| --- | --- | --- |
| 2-[4'-(4''-chlorophenoxy)-phenoxy]-propionic acid | 99.8% | 0.1% |
| 2-[4'-(4''-bromo-2''-chlorophenoxy)-phenoxy]-propionic acid | 99.6% | 0.3% |
| 2-[4'-(4''-chloro-2''-nitrophenoxy)-phenoxy]-propionic acid | 99.5% | 0.4% |
| 2-[4'-(2''-chloro-4''-nitrophenoxy)-phenoxy]-propionic acid | 99.5% | 0.3% |
| 2-[4'-(2'',4''-dichlorobenzyl)-phenoxy]-propionic acid | 99.7% | 0.1% |
| 2-[4'-(2''-chloro-4''-trifluoromethylphenoxy)-phenoxy]-propionic acid | 99.7% | 0.2% |

EXAMPLE 4

D(+)-2-[4'-(2'',4''-Dichlorophenoxy)-phenoxy]-propionic acid 45.7 g (0.57 mol) of sodium hydroxide solution (50% strength) are added at 15° C. to 34.3 g (0.28 mol) of L(−)-2-chloropropionic acid methyl ester ($[\alpha]_D^{23} = -24.7°$, in substance) and 30 ml of water, and stirring is continued for 15 minutes after the addition. The clear solution so obtained is added portionwise at 110°-115° C. to a solution of 63.8 g (0.25 mol) of 4-(2',4'-dichlorophenoxy)-phenol in 300 ml of xylene. During the addition, an inner temperature of 110°-115° C. is maintained by continuous azeotropic distillation of water and methanol. After the addition, stirring is continued at 115° C. for 30 minutes, subsequently 100 ml of water are added at 90° C., stirring is continued for a further 30 minutes at 85° C., the batch is acidified with 25 g of o-phosphoric acid, and the water phase is separated in a separating funnel. After having distilled off the xylene, 81.7 g of D(+)-2-[4'-(2'',4''-dichlorophenoxy)-phenoxy]-propionic acid are obtained. According to gas chromatography, 99.5 % of the intended acid and 0.5% of unreacted phenol are contained therein, corresponding to a yield of 99.5% of th. The acid obtained is esterified with methanol in the presence of sulfuric acid as catalyst. The rotation of (D+)-methyl-2-[4'-(2'',4''-dichlorophenoxy)-phenoxy]-propionate is $[\alpha]_D^{25} = +25.7°$ (1-molar solution in CHCl$_3$), corresponding to an optical purity of 94%.

EXAMPLE 5

D(+)-2-[4'-(2'',4''-Dichlorophenoxy)-phenoxy]-propionic acid 19.8 g of L(−)-2-chloropropionic acid (0.18 mol, 99% strength, mean rotation -15.9°) are added at 15° C. to 30.2 g of 49% sodium hydroxide solution (0.37 mol of sodium hydroxide) and 20 g of ice. The clear solution so obtained is added portionwise at 105° C. to a solution of 38.3 g (0.15 mol) of 4-(2',4'-dichlorophenoxy)-phenol in 300 ml of toluene with continuous azeotropic distillation of water. After the addition, stirring is continued for 30 minutes at 105° C., subsequently 70 ml of water are added at 85° C., stirring is continued for a further 30 minutes at 80° C., the batch is acidified with 15 g of o-phosphoric acid, and the water phase is separated. After having distilled off the toluene, 49 g of D(+)-2-[4'-(2'',4''-dichlorophenoxy)-phenoxy]-propionic acid are obtained having 99.9% of purity according to gas chromatography. The residual content of 4-(2',4'-dichlorophenoxy)-phenol is 0.1%, so that a yield of 99.9% of theory is attained. The acid obtained is esterified with methanol as described in Example 4. Rotation of the (D+)-methyl-2-[4'-(2'',4''-dichlornoxy)-phenoxy]-propionate is $[\alpha]_D^{25} = +24.1°$ (1-molar solution in CHCl$_3$), corresponding to an optical purity of 88%.

EXAMPLE 6

D(+)-2-[4'-(2'',4''-Dichlorophenoxy)-phenoxy]-propionic acid 32.9 g of L(−)-2-chloropropionic acid (99% strength, rotation measured without solvent −15.9°, 23° C.) and 49.6 g of 50% sodium hydroxide solution (0.62 mol of sodium hydroxide) are dosed separately and precisely simultaneously at 110°-115° C. to a solution of 63.8 g (0.25 mol) of 4-(2',4'-dichlorophenoxy)-phenol in 300 ml of xylene; the reaction temperature being maintained by continuous azeotropic distillation of water. After the addition, stirring is continued for 30 minutes at 115° C., subsequently 100 ml of water are added at 90° C., stirring is continued for a further 30 minutes at 85° C., the batch is acidified with 25 g of o-phosphoric acid, and the water phase is eliminated in a separating funnel. After having distilled off the phenol, 81.5 g of D(+)-2-[4'-)2'',4''-dichlorophenoxy)-phenoxy]-propionic acid are obtained. The residual content of unreacted phenol component is 0.2%, corresponding to a yield of 99.7% of theory. The rotation of the D(+)-methyl-2-[2'',4''-dichlorophenoxy)-phenoxy]-propionate obtained therefrom by esterification with methanol is 23.7° $[\alpha]_D^{23} = 23.7°$ (1-molar solution in CHCl$_3$).

EXAMPLE 7

D(+)-2-[4-(4''-Chlorophenoxy)-phenoxy]-propionic acid 49.9 g (0.62 mol) of sodium hydroxide solution (50% strength) are added of 15° C. to 36.8 g (0.3 mol) of L(−)-2-chloropropionic acid methyl ester ($[\alpha]_D^{23} = -23.9°$, in substance) and 40 ml of water, and after the addition, stirring is continued for a further 30 minutes at 15° C. The clear solution obtained is added portionwise at 110°–115° C. to a solution of 55.1 g (0.25 mol) of 4-(4'-chlorophenoxy)-phenol in 300 ml of xylene. An inner temperature of 110°–115° C. is maintained during the addition by continuous azeotropic distillation of water and methanol. The addition being complete, stirring is continued for 30 minutes at 115° C., subsequently 100 ml of water are added at 90° C., stirring is continued for a further 30 minutes at 85° C., the batch is acidified with 25 g of o-phosphoric acid, and the water phase is eliminated in a separating funnel. After having distilled off the xylene, 73.1 g of D(+)-2-[4'-(2'',4''-dichlorophenoxy)-phenoxy]-propionic acid are obtained, in which 99.9% of the intended acid and 0.01% of unreacted phenol are contained according to gas chromatography, which corresponds to a yield of 99.9% of theory. The acid obtained is esterified with methanol in the presence of sulfuric acid as catalyst. Roration of the (D+)-methyl-2-[4'-(4''-chlorophenoxy)-phenoxy]-propionate is $[\alpha]_D^{25} = 24.4°$ (1-molar solution in CHCl₃).

In analogous manner, there were obtained:

| Compound | Yield (% of th.) | Residual amount of starting phenol (wt. %) | rotation of methyl ester (1-molar in CHCl₃) $[\lambda]_D$ | t [°C.] |
|---|---|---|---|---|
| D(+)-2-[4'-(2'',4''-dichlorobenzyl)-phenoxy]-propionic acid | 99.7 | 0.2 | 26.5° | 23 |
| D(+)-2-[4'(4''-trifluoromethylphenoxy)-phenoxy]-propionic acid | 99.9 | 0.1 | +25.2° | 23 |
| D(+)-2-[4'-(4''-trifluoromethyl-2''-chlorophenoxy)-phenoxy]-propionic acid | 99.7 | 0.2 | — | — |
| D(+)-2-[4'-(4''-bromo-2''-chlorophenoxy)-phenoxy]-propionic acid | 99.8 | 0.15 | +23.1° | 23 |

EXAMPLE 8

D-2-[4-(2,4-Dichlorophenoxy)-phenoxy]-propionic acid

A total of 150 g (1.2 mol) of L-2-chloropropionic acid methyl ester (optical purity more than 95%) and a total of 200 g (2.5 mols) of 50 weight % sodium hydroxide solution are added simultaneously from 2 dropping funnels within about 1 hour and with vigorous agitation to a solution of 225 g (1.0 mol) of 4-(2,4-dichlorophenoxy)-phenol in 1,000 ml of xylene preheated to 110° C. Simultaneously with the addition, the mixture of methanol formed and water introduced or formed is removed via a water trap by azeotropic distillation. The reaction is then allowed to proceed for about 30 minutes, the batch is cooled and the D-2-[4-(2,4-dichlorophenoxy)-phenoxy]-propionic acid is set free from the sodium salt precipitated in crystalline form by acidification with dilute sulfuric acid. After separation of the aqueous phase and evaporation of the solvent, 320 g = 98% of theory of crude product are obtained.

Chemical and optical purity are evaluated after conversion to the methyl ester. The D-2-[4-(2,4-dichlorophenoxy)-phenoxy]-propionic acid methyl ester has a chemical purity of more than 95% (GC). The optical rotation is $[\alpha]_D^{23} = 22.0°$ (1 molar in chloroform), corresponding to an optical purity of 79%.

What is claimed is:

1. In a process for the preparation of optically active D-(phenoxy- or benzyl)-phenoxypropionic acids and the alkali metal salts thereof corresponding to the formula I

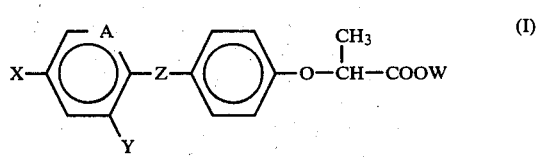

in which
W is hydrogen or an alkali metal cation, and Z is oxygen or CH₂, and in the case where Z is O, X is Cl, Br or CF₃; A is —N═ or CH═; and Y is H or Cl; and in the case where Z is CH₂, X is Cl; A is —CH═ and Y is H or Cl; and their optically active D-isomers by adding to a compound of the formula II

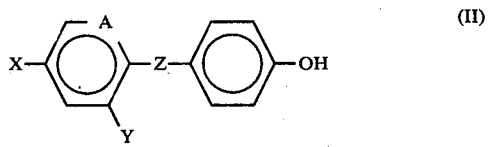

in which A, X Y and Z are defined above, 2-chloropropionic acid or 2-chloropropionic acid lower alkyl ester or the D-isomers thereof in a solvent forming an azeotropic mixture with water and at reflux temperature, the improvement comprising (a) reacting an aqueous alkali hydroxide in double molar amount, relative to the chloropropionic acid component, or a slight excess thereover, and (b) simultaneously distilling off the water introduced or formed during the reaction.

* * * * *